United States Patent
Phillips et al.

(10) Patent No.: US 9,435,189 B2
(45) Date of Patent: Sep. 6, 2016

(54) MONITORING HYDROCARBON FLUID FLOW

(75) Inventors: Raymond Phillips, Bristol (GB); Axel Busboom, Munich (DE); Nicholas Josep Ellson, Bristol (GB); Parag Vyas, Munich (DE)

(73) Assignee: GE Oil & Gas UK Limited, Nailsea (GB)

(*) Notice: Subject to any disclaimer, the term of this patent is extended or adjusted under 35 U.S.C. 154(b) by 387 days.

(21) Appl. No.: 13/469,898

(22) Filed: May 11, 2012

(65) Prior Publication Data
US 2013/0126180 A1 May 23, 2013

(30) Foreign Application Priority Data
May 13, 2011 (EP) .................................... 11166092

(51) Int. Cl.
*E21B 47/00* (2012.01)
*G01N 33/28* (2006.01)

(52) U.S. Cl.
CPC ....... *E21B 47/0001* (2013.01); *G01N 33/2823* (2013.01)

(58) Field of Classification Search
CPC ........... E21B 47/0001; E21B 33/0355; E21B 33/038; E21B 41/0007; E21B 41/04; H02G 9/02
USPC .................. 166/250.01, 386, 368, 254.2; 340/853.1, 853.2, 856.3
See application file for complete search history.

(56) References Cited

U.S. PATENT DOCUMENTS

| | | | | |
|---|---|---|---|---|
| 4,147,222 A | * | 4/1979 | Patten et al. ...................... | 175/9 |
| 4,230,187 A | * | 10/1980 | Seto et al. ..................... | 166/336 |
| 5,741,978 A | * | 4/1998 | Gudmundsson ........... | 73/861.04 |
| 7,210,856 B2 | * | 5/2007 | Ringgenberg .................. | 385/53 |
| 7,938,178 B2 | * | 5/2011 | Ringgenberg et al. .. | 166/250.01 |
| 2001/0027865 A1 | * | 10/2001 | Wester ..................... | 166/250.01 |
| 2008/0042869 A1 | * | 2/2008 | Zimmerman .............. | 340/853.2 |
| 2008/0257032 A1 | * | 10/2008 | Zollo ..................... | E21B 33/03 73/152.29 |
| 2009/0277644 A1 | | 11/2009 | McStay | |
| 2010/0051286 A1 | * | 3/2010 | McStay ................. | E21B 47/123 166/336 |
| 2011/0025526 A1 | | 2/2011 | Simpson | |
| 2011/0040485 A1 | * | 2/2011 | Ong ............................... | 702/12 |

FOREIGN PATENT DOCUMENTS

| | | |
|---|---|---|
| GB | 2456231 A | 7/2009 |
| WO | 2009013695 A1 | 11/2009 |

OTHER PUBLICATIONS

European Search Report from corresponding EP Application No. 11166092.4 dated Jan. 12, 2011.

* cited by examiner

*Primary Examiner* — James G Sayre
(74) *Attorney, Agent, or Firm* — GE Global Patent Operation

(57) ABSTRACT

A method of monitoring a plurality of properties relating to a hydrocarbon fluid flow through a pipeline at a tree for a subsea hydrocarbon extraction facility, the method comprising locating a plurality of sensors at or near a position which is optimum for monitoring the at least one of the plurality of properties in regard to the configuration of the pipeline, the sensors being configured to monitor at least one of the plurality of properties.

19 Claims, 1 Drawing Sheet

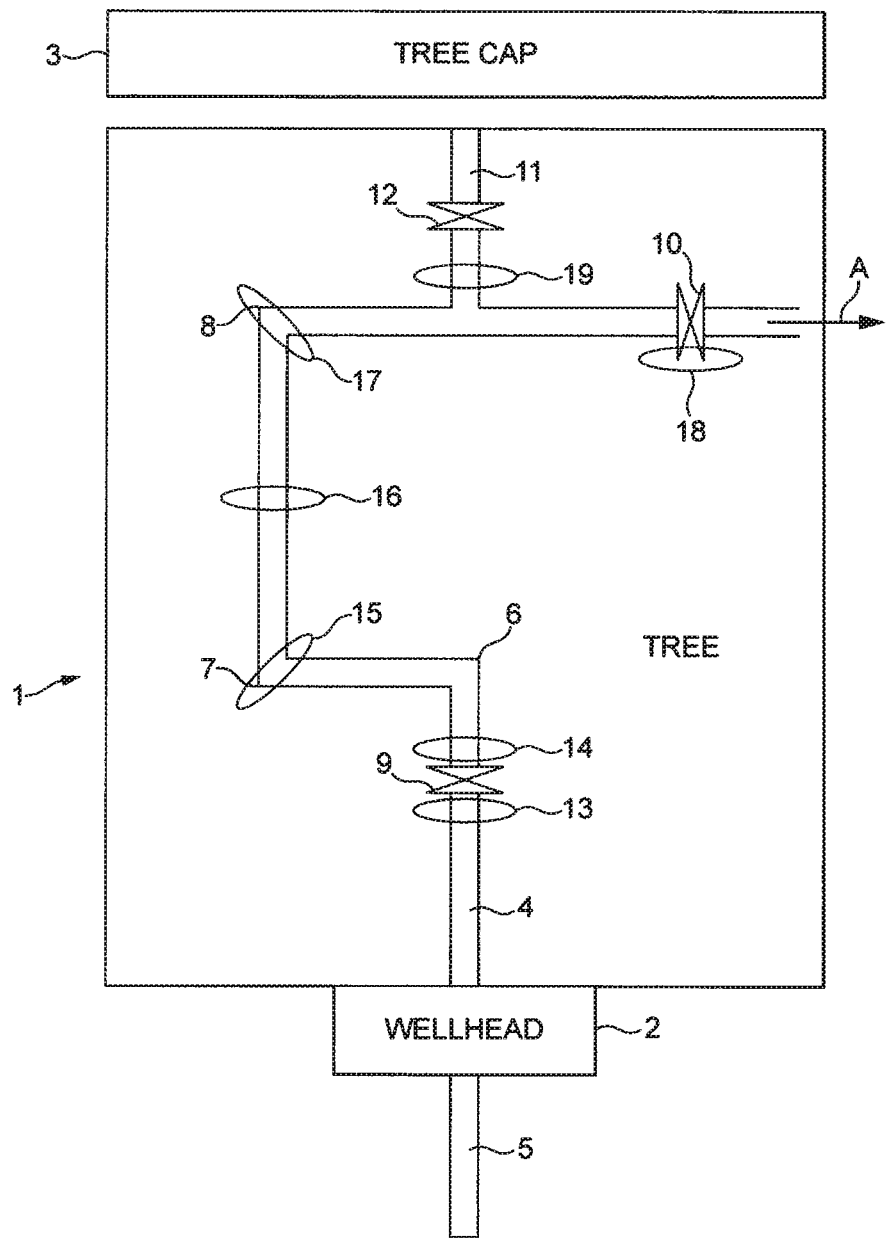

MONITORING HYDROCARBON FLUID FLOW

BACKGROUND OF THE INVENTION

1. Field of the Invention

Embodiments of the present invention relate to monitoring hydrocarbon fluid flow and, more particularly, monitoring hydrocarbon fluid flow at a tree of a subsea hydrocarbon extraction facility.

2. Description of the Prior Art

Hydrocarbon fluid flowing from an offshore reservoir or well is multiphase in nature in that it contains oil, gas and water and can also contain particulates such as sand. Multiphase meters are used to measure the content of gas, oil and water in the fluid, and other sensors are incorporated to measure the particulates. The sensor equipment is normally mounted on a Christmas tree installed on the seabed, and is usually placed on the Christmas tree after the design has been established. Therefore, the sensor location is often dictated by practical issues rather than the optimum positions for measurements. Current practice is to install a multiphase meter on the Christmas tree with a sensor package positioned at a convenient position. The sensor package usually contains a bundle of sensors. Because the sensors are bundled, the individual sensors may not all be ideally positioned to accurately measure their particular parameter. Some fluid flow measurement techniques require the flow to be conditioned (for example, laminar or turbulent) to be at their optimal accuracy. There is a need for a more accurate method of measurement.

One of the most critical aspects of fluid flow is the effect it has on equipment and fluid pipes due to hydrate formation, wax deposition, slugging and corrosion.

These have a serious effect on the efficiency of the fluid flow, equipment lifetime and through-life maintenance requirements, but can be minimized by taking appropriate remedial action, such as the use of chemical injection to clean the surfaces of the fluid pipes. There is a need for accurately identifying, locating and measuring these effects. However, the availability of sufficiently reliable and accurate sensors has limited the ability to provide the required information. Since the positioning of the sensor package on the Christmas tree is decided after the Christmas tree design has been established, the positioning is not optimized.

BRIEF SUMMARY OF INVENTION

According to an embodiment of the present invention, there is provided a method of monitoring a plurality of properties relating to a hydrocarbon fluid flow through a pipeline at a tree for a subsea hydrocarbon extraction facility. The method comprises locating a plurality of sensors at or near a position which is optimum for monitoring the at least one of the plurality of properties in regard to the configuration of the pipeline, the sensors being configured to monitor at least one of the plurality of properties.

According to another embodiment of the present invention, there is provided a tree for a subsea hydrocarbon extraction facility. The tree comprises a plurality of sensors configured to monitor a plurality of properties relating to a hydrocarbon fluid flow through a pipeline at the tree, wherein each of the plurality of sensors is configured to monitor at least one of the plurality of properties, and wherein each of the plurality of sensors is located at or near a position which is optimum for monitoring the at least one of the plurality of properties in regard to the configuration of the pipeline.

BRIEF DESCRIPTION OF THE DRAWINGS

Embodiments of the present invention will be more apparent to those skilled in the art upon reading the following description with reference to the accompanying drawing, in which:

FIG. 1 is a simplified schematic illustration of a subsea Christmas tree according to an embodiment of the present invention.

DETAILED DESCRIPTION OF THE INVENTION

A subsea Christmas tree of a subsea hydrocarbon extraction facility, in its basic form, houses a number of valves for controlling the flow of fluid from a well (such as the main flow control and directional flow valves) together with a subsea control module which enables the valves to be controlled by means of electric or hydraulic actuators. There is also a sensor pack which provides essential data on the state of health of the subsea system and for the provision of data for optimizing the fluid flow from the well.

The physical configuration of the Christmas tree mechanical structure and of the equipment installed results in the flow pipeline, which carries the hydrocarbon fluid, having several sharp bends. These bends can provide optimized positions for some sensor measurements.

FIG. 1 is a simplified schematic illustration showing the main hydrocarbon flow pipeline components and appropriate positions for installing some typical sensors in a tree according to an embodiment of the present invention.

In FIG. 1, a subsea Christmas tree 1 at a wellhead 2 has a tree cap 3 and a flow pipeline 4 fed from production tubing 5. The flow pipeline 4 exits the tree 1 to a flow line in the direction of arrow A and has first, second and third severe or sharp bends 6, 7 and 8. Between the tubing 5 and the first bend 6, the pipeline 4 has a flow control valve 9. Between the third bend 8 and the exit of the flow pipeline 4, the flow pipeline 4 has a directional control valve 10. Between the third bend 8 and directional control valve 10, there is a branch section 11 having a directional control valve 12.

The embodiment of the present invention utilizes the knowledge of the flow regimes in the hydrocarbon flow pipeline 4 and valve configurations on the tree 1 to place suitable discrete sensors in the most appropriate positions to acquire a more accurate overall monitoring of properties relating to hydrocarbon fluid flow. The arrangement of sensors utilizes the physical configuration of the tree 1 and the configuration of the flow pipeline 4 to enable measurements of such properties to be made by using discrete sensors each placed at or near an optimum position in the fluid flow for its measurement in the most meaningful manner.

Typical measurements for which optimum positions (shown in FIG. 1) can be identified on the Christmas tree are described below.

For vibration and/or strain measurement, a sensor 13 can be located at or near flow control valve 9, which could cause vibration, or can be located at a known weak point.

For bulk density measurement, a sensor 14 can be located at or near a point of high turbulence such as after flow control valve 9 or at or near other disruptions.

For particulate detection, such as sand detection, an acoustic sensor 15 can be located at or near the second bend 7 in the flow pipeline 4 to detect particle impact. The acoustic sensor being non-intrusive can be fitted to the outside of the flow pipeline 4.

For ultrasound, electrical impedance spectroscopy, microwave measurements or similar measurements, a sensor 16 can be located between the second bend 7 and the third bend 8 where there is a conditioned steady state flow.

For erosion measurement, a sensor 17 can be located at or near the third bend 8, where there is most serious erosion, to make a direct measurement.

For pressure drop, a sensor 18 which measures pressure drop through a restriction or known change in geometry, such as the pressure drop, can be located across directional control valve 10.

For temperature measurement, a sensor 19 can be placed before directional control valve 12 at or near a most isolated point from any interfering temperature.

Embodiments of the present invention offer a significantly more detailed and accurate method of measuring produced fluid properties compared to conventional methods. Embodiments of the present invention also offer increased functionality for a Christmas tree compared to the conventional approach of integrating instruments attached to a tree as stand-alone instrument packages.

Although embodiments of this invention have been described above with reference to the drawing, those skilled in the art could make numerous alterations to the disclosed embodiments without departing from the spirit or scope of this invention. For example, features shown or described in one embodiment can be applied to another embodiment to form a new embodiment. The particular embodiments described above shall be interpreted as illustrative only and not limiting. All alternative changes that are made on the basis of the description and drawing of the present application are within the scope of the claims.

What is claimed is:

1. A method for monitoring a plurality of properties relating to a hydrocarbon fluid flow through a pipeline at a tree for a subsea hydrocarbon extraction facility, the method comprising:
   locating a plurality of sensors at or near a position for monitoring the at least one of the plurality of properties in regard to the configuration of the pipeline, the sensors being configured to monitor at least one of the plurality of properties; wherein
   a first of the plurality of sensors is located at or near a first side of a valve and is configured to monitor vibration, strain, or both;
   a second of the plurality of sensors is located at or near a second side of the valve and is configured to monitor bulk density in the pipeline; and
   a third of the plurality of sensors located at or near a restriction in the pipeline or at a known change in a geometry of the pipeline and configured to monitor a pressure drop at or near the restriction in the pipeline or at the known change in the geometry of the pipeline.

2. The method according to claim 1, wherein the plurality of sensors comprises at least a fourth sensor configured to monitor at least one of vibration and strain.

3. The method according to claim 1, wherein the plurality of sensors comprises at least a fifth sensor configured to monitor particulates in the hydrocarbon fluid flow, the method further comprising:
   locating the at least a fifth sensor configured to monitor particulates in the hydrocarbon fluid flow at or near a bend in the pipeline.

4. The method according to claim 3, wherein the at least a fifth sensor comprises an ultrasound, electrical impedance spectroscopy, microwave sensor, or any combination thereof, and is configured to measure flow in the pipeline.

5. The method according to claim 1, wherein the plurality of sensors comprises at least a sixth sensor configured to monitor erosion of the pipeline, the method further comprising:
   locating the at least a sixth sensor configured to monitor erosion of the pipeline at or near a bend in the pipeline.

6. The method according to claim 1, wherein the plurality of sensors comprises at least a seventh sensor configured to monitor temperature, the method further comprising:
   locating the at least a seventh sensor configured to monitor temperature at or near a most isolated point from an interfering temperature in or near the pipeline.

7. The method according to claim 1, wherein at least one of the plurality of sensors comprises:
   locating the at least one sensor configured to monitor hulk density at or near a the valve in the pipeline;
   locating the at least one sensor configured to monitor particulates in the hydrocarbon fluid flow at or near a bend in the pipeline;
   locating the at least one sensor configured to monitor temperature at or near a the most isolated point in the pipeline from a predetermined interfering temperature in or near the pipeline.

8. A tree for a subsea hydrocarbon extraction facility, the tree comprising:
   a plurality of sensors configured to monitor a plurality of properties relating to a hydrocarbon fluid flow through a pipeline at the tree, wherein each of the plurality of sensors is configured to monitor at least one of the plurality of properties, and wherein each of the plurality of sensors is located at or near a position for monitoring the at least one of the plurality of properties in regard to the configuration of the pipeline; wherein
   a first of the plurality of sensors is located at or near a first side of a valve and is configured to monitor vibration, strain, or both;
   a second of the plurality of sensors is located at or near a second side of the valve and is configured to monitor bulk density in the pipeline; and
   a third of the plurality of sensors located at or near a restriction in the pipeline or at a known change in a geometry of the pipeline and configured to monitor a pressure drop at or near the restriction in the pipeline or at the known change in the geometry of the pipeline.

9. The tree according to claim 8, wherein the plurality of sensors comprises at least a fourth sensor configured to monitor vibration, strain, or both.

10. The tree according to claim 8, wherein the plurality of sensors comprises at least a fifth sensor configured to monitor particulates in the hydrocarbon fluid flow, wherein the at least a fifth sensor configured to monitor particulates in the hydrocarbon fluid flow is located at or near a bend in the pipeline.

11. The tree according to claim 10, wherein the at least a fifth sensor comprises an ultrasound, electrical impedance spectroscopy, microwave sensor, or any combination thereof, configured to measure flow in the pipeline.

12. The tree according to claim 8, wherein the plurality of sensors comprises at least a sixth sensor configured to monitor erosion of the pipeline, wherein the at least sixth sensor configured to monitor erosion of the pipeline is located at or near a bend in the pipeline.

13. The tree according to claim 8, wherein the plurality of sensors comprises at least a seventh sensor configured to monitor temperature, wherein the at least a seventh sensor configured to monitor temperature is located at or near a most isolated point from an interfering temperature in or near the pipeline.

14. The tree according to claim 8, wherein the plurality of sensors further comprises:
- at least one sensor configured to monitor particulates in the hydrocarbon fluid flow, wherein the at least one sensor configured to monitor particulates in the hydrocarbon fluid flow is located at or near a bend in the pipeline;
- at least one sensor configured to monitor temperature, wherein the at least one sensor configured to monitor temperature is located at or near a region isolated from an interfering temperature.

15. A system for monitoring hydrocarbon flow in a subsea hydrocarbon extraction facility, the system comprising:
- a well head;
- a tree cap;
- a flow pipeline between the wellhead and the tree cap;
- one or more changes in geometry in the flow pipeline;
- one or more valves disposed in the flow pipeline, wherein a first valve comprises a flow control valve between a production tubing feed to the flow pipeline and a first change in geometry in the flow pipeline, a second valve comprises a directional control valve between an exit of the flow pipeline and a third change in geometry in the flow pipeline, and a branch section with another flow control valve between the third change in geometry and the directional control valve;
- at least one first sensor disposed near the flow control valve in the flow pipeline, the at least one first sensor configured to measure one or more of vibration, strain sensor, bulk density or pressure drop; and
- at least one second sensor disposed in the flow pipeline near the third change in geometry of the flow pipeline, the at least one second sensor configured for one or more of particulate detection, ultrasound measurement or erosion measurement.

16. The system according to claim 15, wherein the at least one first sensor is located at a sharp bend in the flow pipeline.

17. The system according to claim 15, wherein the flow pipeline includes a region of steady state flow before or after the one or more changes in geometry, and the at least one second sensor is located in the region of steady state flow.

18. The system according to claim 15, wherein the at least one second sensor is configured to monitor erosion within the flow pipeline.

19. The system according to claim 15, wherein the at least one first sensor is configured to monitor a pressure drop.

* * * * *